(12) United States Patent
Luebke et al.

(10) Patent No.: US 9,718,747 B2
(45) Date of Patent: Aug. 1, 2017

(54) PROCESS FOR HIGH TEMPERATURE REMOVAL OF TRACE CHLORIDE CONTAMINANTS IN A CATALYTIC DEHYDROGENATION PROCESS

(71) Applicant: UOP LLC, Des Plaines, IL (US)

(72) Inventors: Charles P. Luebke, Mt. Prospect, IL (US); Jayant K. Gorawara, Buffalo Grove, IL (US); Vladislav I. Kanazirev, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 231 days.

(21) Appl. No.: 13/922,071

(22) Filed: Jun. 19, 2013

(65) Prior Publication Data

US 2014/0378725 A1    Dec. 25, 2014

(51) Int. Cl.
*C07C 5/327*  (2006.01)
*C07C 7/12*  (2006.01)

(52) U.S. Cl.
CPC ............ *C07C 7/12* (2013.01); *C07C 5/327* (2013.01)

(58) Field of Classification Search
CPC .......... C07C 11/06; C07C 11/02; C07C 6/04; C07C 2521/04; C07C 7/12; C07C 7/13; C07C 7/148; C07C 5/327; C10G 2400/20; C10G 25/003; B01J 20/06
USPC .................................. 585/324, 823
See application file for complete search history.

(56) References Cited

U.S. PATENT DOCUMENTS

| | | | |
|---|---|---|---|
| 4,381,417 A | | 4/1983 | Vora et al. |
| 4,687,649 A | | 8/1987 | Kuroda et al. |
| 5,107,061 A | * | 4/1992 | Ou ........................... A62D 3/34 585/642 |
| 5,254,323 A | | 10/1993 | Itoh et al. |
| 5,481,060 A | * | 1/1996 | Scott et al. ................. 585/867 |
| 5,645,713 A | | 7/1997 | Yan |
| 5,672,804 A | * | 9/1997 | Glover .................... C07C 7/005 585/655 |
| 5,792,899 A | * | 8/1998 | Cottrell ..................... C07C 7/12 568/697 |
| 5,849,979 A | * | 12/1998 | Kalnes ..................... C07C 7/11 585/655 |
| 6,060,033 A | * | 5/2000 | Cheng ....................... 423/240 S |
| 6,200,544 B1 | * | 3/2001 | Blachman ................ 423/240 R |
| 6,719,957 B2 | | 4/2004 | Brady, Jr. et al. |
| 6,784,132 B1 | | 8/2004 | Sechrist |
| 7,439,410 B1 | | 10/2008 | Rice et al. |
| 2006/0252642 A1 | * | 11/2006 | Kanazirev ............. B01D 53/02 502/415 |

(Continued)

OTHER PUBLICATIONS

PCT International Search Report for PCT/US2014/042043 mailed Sep. 25, 2014.

(Continued)

*Primary Examiner* — In Suk Bullock
*Assistant Examiner* — Aaron Pierpont (57) ABSTRACT

A process for removal of trace chloride contaminants from a reactor effluent in a catalytic dehydrogenation process is described. The reactor effluent is compressed in a compressor to provide a compressed effluent. The compressed effluent is introduced from the compressor into a chloride treater. In the chloride treater, trace chloride contaminants in the compressed effluent are adsorbed to provide a treated effluent. The treated effluent is cooled in a cooler.

14 Claims, 3 Drawing Sheets

(56) References Cited

U.S. PATENT DOCUMENTS

2010/0222215 A1 9/2010 Kanazirev
2011/0144397 A1* 6/2011 van Egmond et al. ....... 585/256

OTHER PUBLICATIONS

Search Report dated Dec. 16, 2016 for corresponding EP Application No. 14813480.2.

* cited by examiner

PROCESS FOR HIGH TEMPERATURE REMOVAL OF TRACE CHLORIDE CONTAMINANTS IN A CATALYTIC DEHYDROGENATION PROCESS

BACKGROUND OF THE INVENTION

Catalytic dehydrogenation can be used to convert paraffins to the corresponding olefin, e.g., propane to propene, or butane to butene.

Figure 1:
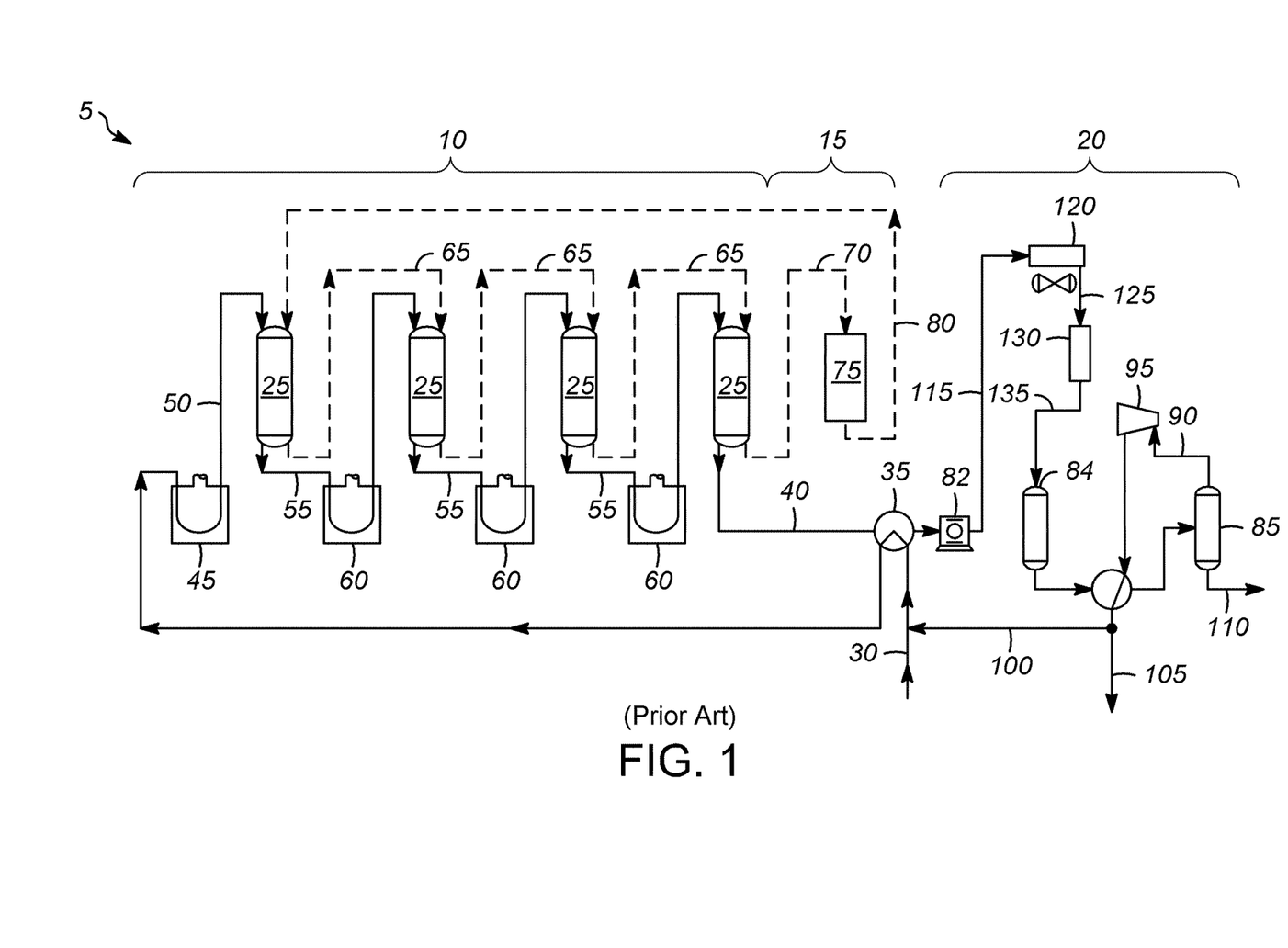
FIG. 1 is an illustration of a conventional trace chloride contaminant removal process for reactor effluent in a catalytic dehydrogenation process.

FIG. 1 shows one typical arrangement for a catalytic dehydrogenation process 5. The process 5 includes a reactor section 10, a catalyst regeneration section 15, and a product recovery section 20.

The reactor section 10 includes one or more reactors 25 (four are shown in FIG. 1). A hydrocarbon feed 30 is sent to a heat exchanger 35 where it exchanges heat with a reactor effluent 40 to raise the feed temperature. The feed 30 is sent to a preheater 45 where it is heated to the desired inlet temperature. The preheated feed 50 is sent from the preheater 45 to the first reactor 25. Because the dehydrogenation reaction is endothermic, the temperature of the effluent 55 from the first reactor 25 is less than the temperature of the preheated feed 50. The effluent 55 is sent to interstage heaters 60 to raise the temperature to the desired inlet temperature for the next reactor 25.

After the last reactor (in this example, the fourth reactor), the reactor effluent 40 is sent to the heat exchanger 35, and heat is exchanged with the feed 30. The reactor effluent 40 is then sent to the product recovery section 20.

The catalyst 65 moves through the series of reactors 25. When the catalyst 70 leaves the last reactor 25, it is sent to the catalyst regeneration section 15. The catalyst regeneration section 15 includes a reactor 75 where coke on the catalyst is burned off and the catalyst may go through a reconditioning step. A regenerated catalyst 80 is sent back to the first reactor 25.

As will be appreciated by those of ordinary skill in the art, the organic chloride used to condition paraffin dehydrogenation catalysts results in undesirable chlorinated species (chloride) compounds, such as HCl and organic chlorides (RCl), in the reactor effluent. Such compounds are referred to herein as trace chloride contaminants. Example deleterious effects from untreated trace chloride contaminants include corrosion, poisoning of downstream catalysts, and other effects. Accordingly, product recovery in typical catalytic dehydrogenation processes includes a process for removal of trace chloride contaminants.

For example, FIG. 1 shows a typical chloride removal process that is integrated into the product recovery section 20. The reactor effluent 40 is compressed in the compressor 82. The compressed effluent 115, which typically occurs at a temperature of about 110-177° C. (230-350° F.) when exiting the compressor 82 (e.g., via a discharge drum), is introduced to a cooler 120, for instance a heat exchanger. The cooler 120 lowers the temperature of the compressed effluent to about 25-60° C. and in some examples 38-60° C. (100-120° F.). The cooled effluent 125 (cooled product stream) is then introduced into a chloride remover 130, such as a chloride scavenging guard bed. The chloride remover 130 includes an adsorbent, which adsorbs chlorides from the cooled effluent 125 and provides a treated effluent 135. Treated effluent 135 is introduced to a drier 84. The drier 84 can be a reactor effluent drier system (RED) for drying and purification, including water and hydrogen sulfide ($H_2S$) removal.

An example reactor effluent dryer (RED) system includes two or more adsorbent beds arranged in a typical thermal swing adsorption (TSA) system. While one or more adsorbent beds is in adsorption mode to purify and dehydrate the process stream, the other bed(s) are in regeneration mode. When the adsorbent bed(s) in the adsorption step starts to breakthrough the contaminants, the bed(s) on adsorbent mode is switched to regeneration mode and the freshly regenerated bed(s) are placed in adsorption mode. The beds are switched between adsorption and regeneration modes to provide for continuous purification of the process stream. Regeneration of the adsorbents is accomplished by purging the beds with a regenerant stream such as an inert gas, net gas, or vaporized hydrocarbon stream, at elevated temperature to desorb the impurities and water to rejuvenate the adsorbent and prepare it for a fresh adsorption step. The TSA process is well known to those skilled in the art.

The dried effluent is separated in separator 85. Gas 90 is expanded in expander 95 and separated into a recycle hydrogen stream 100 and a net separator gas stream 105. A liquid stream 110, which includes the olefin product and unconverted paraffin, is sent for further processing, where the desired olefin product is recovered and the unconverted paraffin is recycled to the dehydrogenation reactor 25.

An example chloride scavenging guard bed for the chloride treater 130 includes a vessel having one or more chloride scavenging adsorbents, referred to as guard beds. Examples of adsorbents include activated alumina, promoted aluminas, metal oxides, zeolite-based adsorbents, and others. The cooled compressed effluent 125 passes through the vessel, and over the beds, contacting the adsorbent to remove chloride contaminants. It is possible that both physical and chemical adsorption may take place.

A significant amount of heavy hydrocarbon residue that is present in the reactor effluent 40 enters the chloride treater 130. The heavy hydrocarbon residue is a result of undesirable side reactions occurring primarily in the reactor section 10 of the catalytic dehydrogenation unit. Examples of heavy hydrocarbons include polynuclear aromatics. The heavy hydrocarbon residue, a known impurity, negatively affects the performance of the chloride treater adsorbent. While a solvent, such as para-diethylbenzene or light cycle oil, can be provided to clean the reactor effluent 40 and the cooler 120, hydrocarbon residue still is present in feed to the chloride remover 130 or the reactor effluent driers 84.

If a reactive adsorbent is employed in a highly reactive hydrocarbon stream, such as that present in the catalytic dehydrogenation process, undesirable reactions, such as polymerization, alkylation, etc. can result in formation of high molecular weight heavier hydrocarbons. These heavy hydrocarbons can deposit on the adsorbent surfaces, filling up pore volume and creating mass transfer resistance by forming liquid film around adsorbent particles, thereby reducing capacity of the adsorbent. To compensate for such effects, it may be possible to increase the surface to volume ratio of the adsorbent particle by use of higher external surface area particles or reducing the particle size of the adsorbent. However, such strategies are not very effective, and may result in increased cost of production. In addition, reducing the adsorbent particle size will result in an undesirably large pressure drop across the chloride remover 130.

SUMMARY OF THE INVENTION

One aspect of the invention involves a process for trace chloride contaminant removal of a reactor effluent in a catalytic dehydrogenation process. The reactor effluent is compressed in a compressor to provide a compressed effluent. The compressed effluent is introduced from the compressor into a chloride remover. Chlorides present in the compressed effluent are adsorbed in the chloride remover to provide a treated effluent. The treated effluent is subsequently cooled in a cooler.

Another aspect of the invention involves a process for high temperature trace chloride contaminant removal of a reactor effluent in a catalytic dehydrogenation process. A hydrocarbon feed in a dehydrogenation reaction zone is dehydrogenated under dehydrogenation reaction conditions in the presence of a dehydrogenation catalyst to form a reactor effluent. The reactor effluent is compressed to provide a compressed effluent. The compressed effluent is introduced into a chloride remover at a temperature that is above a dew point of the compressed effluent. Trace chloride contaminants present in the compressed effluent are adsorbed in the chloride remover with an adsorbent to provide a treated effluent. The treated effluent is cooled.

DETAILED DESCRIPTION OF THE INVENTION

The propensity for undesirable side reactions over a chloride adsorbent, such as acid catalyzed polymerization, oligomerization, cyclization, and heavy residue formation by condensation, typically increases at higher temperatures. Further, it was believed that higher temperatures unduly reduce adsorbent capacity of the adsorption process. It was thought that the best performance for the chloride remover could be achieved with a cooled product stream from the cooler downstream of the reactor effluent compressor in a catalytic dehydrogenation unit. Thus, conventionally, the chloride remover has been located downstream of the compressor and downstream of the cooler to enable an increased capacity of the adsorbent, as shown in FIG. 1.

However, if there is an available adsorbent with suitable properties, such as low reactivity towards olefin polymerization and high capacity at elevated temperatures of operation, it is better to locate the chloride remover on a hotter stream before the cooler. This hotter stream reduces adsorbent fouling caused by condensation of heavy hydrocarbons and boosts the kinetics of the chloride removal process, providing higher chloride removal capacity and better utilization of the active component of the adsorbent.

An example embodiment of the present invention involves a process for trace chloride contaminant removal of a reactor effluent in a catalytic dehydrogenation process.

Figure 2:
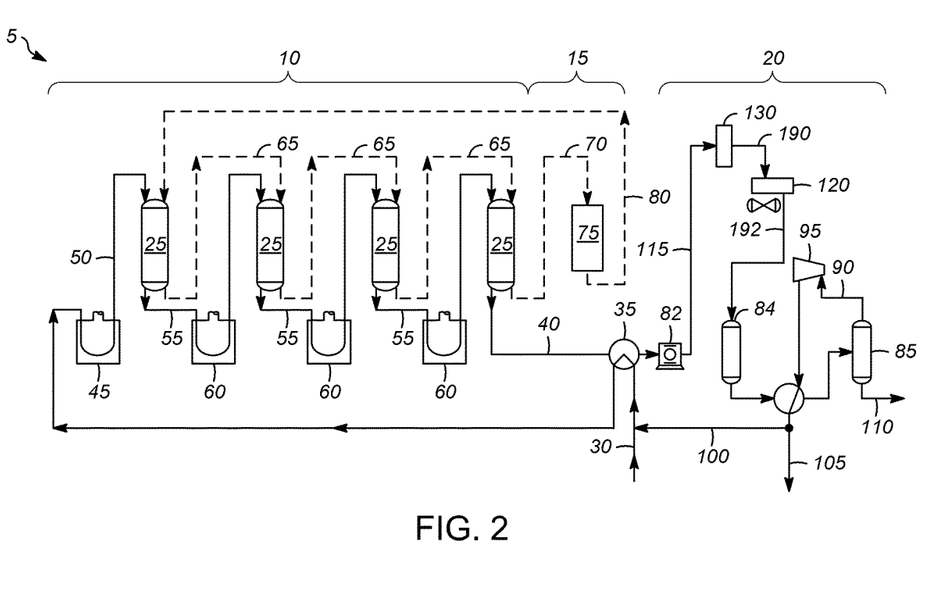
FIG. 2 is an illustration of an embodiment of a trace chloride contaminant removal process for reactor effluent in a catalytic dehydrogenation process.

An example catalytic dehydrogenation process for which an embodiment trace chloride contaminant removal process can be employed is shown in FIG. 2, though other processes will be apparent to those of ordinary skill in the art. The reactor effluent is compressed in a compressor to provide a compressed effluent. Compression includes increasing a pressure of the reactor effluent. The compressed effluent is introduced from the compressor into a chloride remover. In the chloride remover, chloride present in the compressed effluent is adsorbed to provide a treated effluent. The treated effluent is then cooled in a cooler.

The compressed effluent can be introduced directly from the compressor into the chloride remover. By "directly," it is intended that the compressed effluent be introduced without entering into an intervening process component that provides a significant change in the composition or pressure of the compressed effluent. A suitable fluid line between the compressor and the chloride remover can be used and still provide a "direct" introduction to the chloride remover. In another example, the temperature of the compressed effluent can be adjusted, such as by a heater or cooler disposed between the compressor and the chloride remover, to a sufficiently high level to reduce or prevent condensation or fouling, yet low enough to reduce or prevent polymerization reactions. This temperature can be optimized in an example embodiment.

The chloride adsorption can take place at a temperature that is above the dew point temperature of the incoming stream (e.g., the compressed effluent) at the particular process conditions. This temperature in an example process is between about 93-300° C. (about 200-572° F.), more preferably between about 93-177° C. (about 200 to about 350° F.), and most preferably between about 121-177° C. (about 250-350° F.), though in some processes temperatures above 200° C. can also increase the side reactions of the main (olefinic) stream, which can lead to adsorbent fouling.

The chloride adsorption can comprise contacting the compressed effluent with an adsorbent, wherein chloride is adsorbed. The adsorption process can involve physical adsorption, chemisorption, and chemical reaction.

The adsorbent material has a low catalytic activity for olefinic hydrocarbons to limit side reactions and fouling events in the chloride remover. The adsorbent can comprise activated alumina, a promoted alumina product, a highly promoted alumina, metal oxides or suitable molecular sieves, or a combination thereof. Activated alumina is a highly porous material manufactured by dehydroxylating aluminum hydroxide. Promoted alumina refers to impregnating or doping the alumina, for instance with sodium carbonate, sodium hydroxide, or calcium hydroxide, to cause the alumina to absorb more chlorides, and highly promoted alumina refers to at least about 3 wt % as alkaline oxide as an amount of impregnation or doping.

A pressure of the compressed effluent can be between about 345 kPa to about 2750 kPa (about 50 to about 400 psig).

The cooled effluent can be introduced into a drier. The cooling of the treated effluent takes place downstream of the chloride remover and upstream of the drier.

Another inventive aspect includes a process for high temperature trace chloride contaminant removal from a reactor effluent in a catalytic dehydrogenation process. A hydrocarbon feed is dehydrogenated in a dehydrogenation reaction zone, such as the reactor section 10. The dehydrogenation takes place under dehydrogenation reaction conditions in the presence of a dehydrogenation catalyst to form a reactor effluent. The reactor effluent is compressed to provide a compressed effluent. The compressed effluent is introduced into a chloride remover at a temperature that is above the dew point temperature of the incoming stream (e.g., the compressed effluent 115, either directly or via a heater or cooler). In an example process, this temperature is between about 93-300° C. (about 200-572° F.), more preferably between about 93-177° C. (about 200 to about 350° F.), and most preferably between about 121-177° C. (about 250-350° F.). This high temperature can be provided by introducing a reactor effluent to a chloride treater either directly or after adjusting the temperature via a heater or cooler. Trace chloride contaminants present in the compressed effluent are adsorbed in the chloride remover with an adsorbent to provide a treated effluent. The treated effluent is cooled.

The cooled effluent can be introduced into a drier. The cooling of the treated effluent takes place downstream of the chloride remover and upstream of the drier.

In an embodiment, an olefin product, an unconverted paraffin, and a recycle hydrogen stream are separated from an output stream of the drier. The olefin product is recovered. The recycle hydrogen stream and the unconverted paraffin are recycled to the dehydrogenation reaction zone.

Referring now to FIG. 2, the hydrocarbon feed 30 is dehydrogenated in a dehydrogenation zone provided by the reactor section 10. The dehydrogenation of paraffinic hydrocarbons is well known to those skilled in the art of hydrocarbon processing. In the dehydrogenation process, the fresh hydrocarbon feed 30 is combined with recycle hydrogen and unconverted hydrocarbons. Dehydrogenatable hydrocarbons preferably include isoalkanes having 3 or 5 carbon atoms. A suitable feed of dehydrogenatable hydrocarbons will often contain light hydrocarbons (i.e., those having less carbon atoms than the primary feed components) which, for the purpose of reaction, serve as contaminants. In most cases, olefins are excluded from the dehydrogenation zone recycle in order to avoid the formation of dienes which produce unwanted by-products in many of the olefin conversion processes. Along with the dehydrogenatable hydrocarbons, the feed 30 to the reactor section 10 comprises an $H_2$-rich stream, preferably containing at least 75 mol % $H_2$. The $H_2$ acts to suppress the formation of hydrocarbonaceous deposits on the surface of the catalyst, more typically known as coke, and can act to suppress undesirable thermal cracking. Because $H_2$ is generated in the dehydrogenation reaction and comprises a portion of the effluent, the $H_2$-rich stream introduced into the reactor section 10 generally comprises recycle $H_2$ derived from separation of the reactor effluent 40. Alternately, the $H_2$ may be supplied from suitable sources other than the reactor effluent 40.

The combined stream of hydrogen and hydrocarbons is passed through the reactors 25, which include a suitable bed of dehydrogenation catalyst maintained at the proper dehydrogenation conditions such as temperature, pressure and space velocity. The reactor effluent 40 from the reactor section 10 is processed further to yield a stream of olefinic hydrocarbons.

The dehydrogenation reaction is a highly endothermic reaction which is typically effected at low (near atmospheric) pressure conditions. The precise dehydrogenation temperature and pressure employed in the dehydrogenation reaction zone will depend on a variety of factors, such as the composition of the paraffinic hydrocarbon feedstock, the activity of the selected catalyst, and the hydrocarbon conversion rate. In general, dehydrogenation conditions include a pressure of from about 0 MPa (0 bar) to about 3.5 MPa (35 bars) and a temperature of from about 480° C. (900° F.) to about 760° C. (1400° F.). The suitable hydrocarbon feed 30 is charged to the reactors 25 and contacted with the catalyst contained therein at an LHSV of from about 1 to about 10. Hydrogen, principally recycle hydrogen, is suitably admixed with the hydrocarbon feed 30 in a mole ratio of from about 0.1 to about 10. Preferred dehydrogenation conditions, particularly with respect to $C_3$-$C_5$ paraffinic hydrocarbon feedstocks, include a pressure of from about 0 MPa (0 bar) to about 0.5 MPa (5 bars) and a temperature of from about 540° C. (1000° F.) to about 705° C. (1300° F.), a hydrogen-to-hydrocarbon mole ratio of from about 0.1 to about 2, and an LHSV of less than 4.

The dehydrogenation may use any suitable dehydrogenation catalyst. Generally, preferred suitable catalyst comprises a Group VIII noble metal component (e.g., platinum, iridium, rhodium, and palladium), an alkali metal component, and a porous inorganic carrier material. The catalyst may also contain promoter metals which advantageously improve the performance of the catalyst. The porous carrier material should be relatively refractory to the conditions utilized in the reactor section 10 and may be chosen from those carrier materials which have traditionally been utilized in dual function hydrocarbon conversion catalysts. A preferred porous carrier material is a refractory inorganic oxide, with the most preferred an alumina carrier material. The particles are usually spheroidal and have a diameter of from about 1/16 to about 1/8 inch (about 1.6 to about 3.2 mm), although they may be as large as about 1/4 inch (about 6.4 mm).

Operation of the reactor section 10 will produce a mixture of hydrogen and hydrocarbons. Normally, a portion of the hydrocarbons will include an equilibrium mixture of the desired olefin and its alkane precursor. The reactor effluent 40 from the reactor section 10 passes to the product recovery section 20. The product recovery section 20 removes hydrogen from the reactor effluent 40 and recovers it in high purity for recycle to the reactor section 10. Separation steps for the removal of hydrogen will normally include cooling and compressing with subsequent cooling and flashing in a separation vessel. Such methods for the separation of hydrogen and light gases are well known by those skilled in the art.

A typical dehydrogenation process passes the combined hydrocarbon and hydrogen feed through the plurality of reactors 25 with interstage heating between the reactors provided by the interstage heaters 60. The feed 30 including hydrocarbons and hydrogen is initially heated by indirect heat exchange 35 with the reactor effluent 40 from the reactor section 10. Following heating, the feed 30 normally passes through the preheater 45 to further increase the temperature of the feed components before it enters the reactors 25 where it is contacted with the dehydrogenation catalyst. The endothermic reaction reduces the temperature of the reactants which then undergo interstage heating at the interstage heaters 60 before entering the next reactor. After the heat exchange 35 with the feed 30, the reactor effluent 40 from the last reactor 25 passes to the product recovery section 20.

In the product recovery section 20, the reactor effluent 40 is compressed in the compressor 82 to provide a compressed effluent. The compressed effluent 115 is either introduced directly into a chloride remover 130, as shown in FIG. 2, or is passed through a cooler or heater to adjust the temperature of the compressed effluent 115, to a temperature that is above the dew point temperature of the compressed effluent stream 115 at the particular process conditions. In an example embodiment, this temperature is between about 93-300° C. (about 200-572° F.), more preferably between about 93-177° C. (about 200 to about 350° F.), and most preferably between about 121-177° C. (about 250-350° F.). In the chloride remover 130, chloride present in the compressed effluent 115 is adsorbed with an adsorbent to provide a treated effluent 190.

In an embodiment, the adsorbent has a low hydrocarbon reactivity. "Low hydrocarbon reactivity" refers to a strongly reduced susceptibility of the adsorbent material to catalyze side reactions of the main stream (e.g., the compressed effluent 115) upon formation of undesirable side products and fouling components which jeopardize the product purity and adsorbent effectiveness.

In an example embodiment, the treated effluent 190 is cooled at the cooler 120, which in FIG. 2 is downstream of the chloride removal. In an embodiment, cooling the treated effluent 190 cools the treated effluent to a temperature of between about 25-50° C.

The present inventors have observed that heavy hydrocarbons such as polynuclear aromatics condense from a process stream at lower temperatures (e.g., about 38-49° C. (about 100-120° F.)) and form a layer of deposit on the adsorbent of the chloride remover 130, fouling the adsorbent. This fouling reduces the capacity of the adsorbent, for instance by two thirds to a half of the maximum capacity. The result is poor chloride capacity in the chloride remover 130.

To avoid fouling the absorbent, the chloride remover 130 can be located at a higher temperature that is above the dew point temperature of the process stream at the particular process conditions, which lowers the degree of condensation. An example higher temperature is between about 93-300° C. (about 200-572° F.), more preferably between about 93-177° C. (about 200 to about 350° F.), and most preferably between about 121-177° C. (about 250-350° F.). In a particular example, this higher temperature can be located at the discharge of the compressor 82, as shown in FIG. 2. This higher temperature reduces or prevents the condensation of heavy hydrocarbons.

By selecting and using a high capacity chloride adsorbent that is operable at elevated temperatures and that has a low hydrocarbon reactivity, the chloride removal performance can be improved from that of traditional adsorbent placed downstream of the cooler 120 in FIG. 1, even at higher temperatures. In addition, an optimum chloride adsorbent will have the additional property of no or low reduction in capacity at the higher proposed operating temperature. This provides a surprising result in that it allows the chloride remover 130 to be located upstream of the cooler 120 on a hotter stream, e.g., at the discharge of the compressor 82. This results in high chloride loading and better adsorbent life.

The reactor effluent 40 in an example embodiment contains unconverted saturated hydrocarbons, olefin hydrocarbons, mononuclear aromatic compounds in an amount from about 100 to about 5,000 wppm, and polynuclear aromatic compounds in an amount from about 5 to about 500 wppm. This reactor effluent 40 is compressed in compressor 82. The compressed effluent 115 at the discharge of the compressor 82, e.g., from a compressor discharge drum, is introduced into the chloride remover 130. For a C3 catalytic dehydrogenation process, the compressed effluent 115 can be at a temperature that is between about 93-300° C. (about 200-572° F.), more preferably between about 93-177° C. (about 200 to about 350° F.), and most preferably between about 121-177° C. (about 250-350° F.). Other temperature ranges are possible for the compressed effluent 115, for instance depending on the particular catalytic dehydrogenation process (e.g., C4, C5).

An example pressure for the compressed effluent 115 that is introduced into the chloride remover 130 is about 345 kPa to 2750 kPa (about 50 psig to 400 psig), and in a particular example embodiment is about 1450 kPa (about 210 psig). The pressure of the reactor effluent 40 before the compressor 82 is typically too low (e.g., only about 7 kPa (1 psig)) and it is not practical to locate the chloride remover 130 at this location. However, it is possible that the chloride remover 130 could be located before the compressor 82 if the catalytic dehydrogenation process is performed at a higher pressure, though this lower pressure could impact olefin conversion in the catalytic dehydrogenation reactors 25.

As shown in FIG. 2, in a particular example embodiment, the compressed effluent 115 is directly introduced as an incoming stream into the chloride remover 130, without first cooling the compressed effluent. This provides both a suitable temperature and pressure of the compressed effluent 115 for operation of the chloride remover 130. In another embodiment, a cooler or heater (not shown) can be disposed in the process between the compressor 82 and the chloride remover 130 to adjust (raise or lower) the temperature of the compressed effluent 115 to a selected (e.g., an optimal) temperature that is above the dew point temperature of the incoming stream at the particular process conditions.

The chloride remover 130 can be configured similarly to the chloride remover 130 in FIG. 1, or can be otherwise configured. In an example embodiment shown in FIG. 3, the chloride remover 130 is a non-regenerative chloride remover including a vessel 160 and scavenging guard beds 162 disposed therein that includes one or more adsorbents, which are typically formed as extrudates or beads. An inlet distributor 164 is provided at a top of the vessel 160, and inert support media 166, 168 (e.g., ceramic support balls) are disposed above and below the adsorbent material, respectively, to provide for optimal flow distribution. In an example embodiment, the support media 166 above the adsorbent material guard beds 162 includes 19 mm balls 169 disposed on a screen 170, and the support media 168 below the adsorbent material guard beds includes layers 172, 174, 176 (higher to lower) of 3 mm balls, 6 mm balls, and 19 mm balls disposed on a support screen 178, which is disposed above an outlet 180. The support media 166, 168 may be of other sizes, as will be appreciated by those of ordinary skill in the art.

An example chloride adsorbent is a shaped particle (such as beads or pellets) in a suitable size to allow for good flow distribution while managing the pressure drop to a low level. The typical adsorbent particle size used in the catalytical dehydrogenation process is of a nominal particle diameter of 3.2 mm (⅛ inch), although it is contemplated for other example processes to use a larger or smaller size also. For promoted alumina adsorbents, as the adsorbents pick up chloride, the promoter and the aluminum react with the chloride to form salts.

An example adsorbent that can be used is in the class of promoted alumina products, such as but not limited to highly promoted alumina. Example highly promoted alumina contains sodium (Na) from about 1-28 wt % calculated as an oxide, and in a more particular example contains Na from about 3-18 wt %. Example highly promoted alumina adsorbents that can be used are disclosed in U.S. Pat. No. 7,758,837 and in US Patent Application Publication No. 2010/0222215. A particular example highly promoted alumina adsorbent is CLR-204, manufactured by UOP, of Des Plaines, Ill. CLR-204 has properties of low reactivity (e.g., no measurable changes in the stream composition at temperatures of 200° C. or higher), as compared to traditional adsorbent, and high capacity (e.g., 14%) at elevated temperatures (e.g., 200° C.).

Other activated aluminas can also be used as the chloride adsorbent, though olefin reactivity and hence fouling effects can be a consideration. Other chloride absorbent such as metal oxide/metal carbonate products can also be used, provided a sufficient surface area is provided to maximize chloride capacity. Example metal oxides include ZnO, MgO, CaO, and combined products. Another example of an adsorbent that can be used is a molecular sieve adsorbent such as natural and synthetic zeolites modified to reduce catalytic reactivity. An example molecular sieve adsorbent material is a sodium faujisite.

Figure 3:
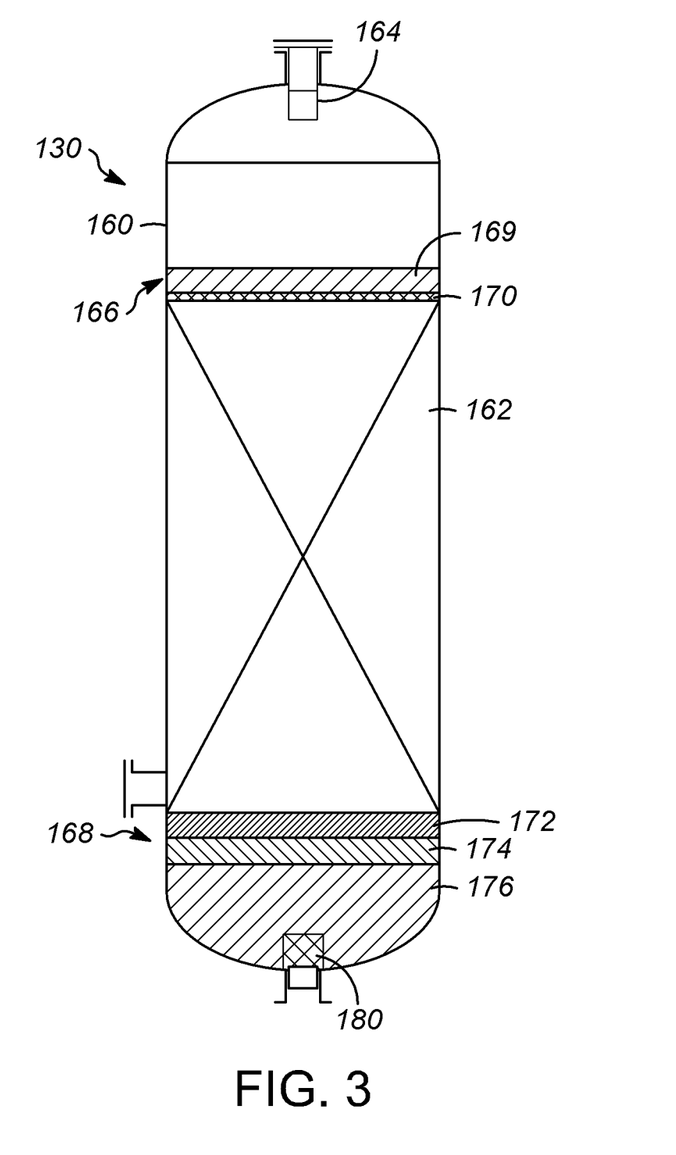
FIG. 3 is an illustration of a chloride remover for use in an example trace chloride contaminant removal process.

In an example operation of the chloride remover 130, the compressed effluent 115, at a temperature between about 93-300° C. (about 200-572° F.), more preferably between about 93-177° C. (about 200 to about 350° F.), and most preferably between about 121-177° C. (about 250-350° F.), passes through the vessel 160, through the support media 166, 168, and over the adsorbent guard bed 162. Both physical and chemical adsorption take place in the guard bed 162 as the adsorbent contacts the compressed effluent 115, removing trace chloride contaminants from the compressed effluent.

Referring again to FIG. 2, operation of the chloride remover 130 results in the treated effluent 190. In an example process, the treated effluent 190 is introduced to the cooler 120, which is located downstream of the chloride remover 130 and upstream of the drier 84. An example cooler 120 is a heat exchanger. An example operation of the cooler 120 lowers the temperature of the treated effluent 190 to a range of about 38-49° C. (about 100-120° F.). The cooled effluent 192 is then introduced to the drier 84. Operation of the drier 84 can be as described above, or in other ways as will be appreciated by those of ordinary skill in the art.

The drier 84 output stream is separated in separator 85. Gas 90 is expanded in expander 95 and separated into a recycle hydrogen stream 100 and a net separator gas stream 105. A liquid stream 110, which includes the olefin product and unconverted paraffin, is sent for further processing, where the desired olefin product is recovered and the unconverted paraffin is recycled to the dehydrogenation reactors 25.

Thus, the example chloride remover 130 in FIG. 3 is located upstream of the cooler 120 and downstream of the compressor 82. Locating the chloride remover 130 upstream of the cooler 120 provides the advantage that there is less heavy hydrocarbon deposition. This also makes the chloride remover 130 easier to unload. By contrast, in some conventional processes, agglomeration of heavy hydrocarbons makes the chloride remover difficult to unload. Further, if adsorbents such as CLR-204 are used, the chloride remover 130 can be unloaded as non-hazardous material.

By placing the chloride remover 130 just downstream of the compressor 82 in the chloride removal process, the compressed effluent 115 can be hot enough to prevent or minimize condensation of heavy hydrocarbons from the reactor effluent 40 which would cause absorbent fouling. Further, the temperature of the compressed effluent 115 can be cold enough to reduce or prevent byproducts such as heavy hydrocarbons from polymerizing and forming coke in the chloride remover 130.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for removal of trace chloride contaminants in a reactor effluent in a catalytic dehydrogenation process, the process comprising:
   compressing the reactor effluent, comprising trace chloride contaminants, hydrocarbons having 3 to 5 carbon atoms and from about 5 to 500 wppm polynuclear aromatics, in a compressor to provide a compressed effluent;
   cooling or heating the compressed effluent to a temperature above the dew point of the compressed effluent, but below polymerization temperatures of the compressed effluent, to produce a cooled or heated compressed effluent, wherein the temperature to which the compressed effluent is cooled or heated is between 93° C. and 300° C.;
   introducing the cooled or heated compressed effluent into a chloride remover;
   adsorbing trace chlorides contaminants present in the cooled or heated compressed effluent in the chloride remover, to provide a treated effluent; and
   cooling the treated effluent in a cooler to produce a cooled treated effluent.

2. The process of claim 1, wherein adsorbing the chlorides takes place at a temperature between about 121° C. and 177° C.

3. The process of claim 1, wherein adsorbing the chlorides comprises:
   contacting the cooled or heated compressed effluent with an adsorbent material.

4. The process of claim 3, wherein adsorbing the chlorides comprises physical adsorption, chemisorption, or a combination thereof.

5. The process of claim 3, wherein the adsorbent material comprises activated alumina, a promoted alumina product, metal oxides, molecular sieves, or a combination thereof.

6. The process of claim 3, wherein the adsorbent material comprises a highly promoted alumina.

7. The process of claim 1, further comprising:
   introducing the cooled treated effluent to a drier;
   wherein cooling the treated effluent takes place downstream of the chloride remover and upstream of the drier.

8. The process of claim 1, wherein the pressure of the compressed effluent is between about 345 kPa and 2750 kPa.

9. A process for removal of trace chloride contaminants from a reactor effluent in a catalytic dehydrogenation process, the process comprising:
   dehydrogenating a hydrocarbon, feed comprising hydrocarbons having 3 to 5 carbon atoms in a dehydrogenation reaction zone under dehydrogenation reaction conditions in the presence of a dehydrogenation catalyst to form a reactor effluent comprising trace chloride contaminants, hydrocarbons having 3 to 5 carbon atoms and from about 5 to 500 wppm polynuclear aromatics;
   compressing the reactor effluent to provide a compressed effluent;
   introducing the compressed effluent into a chloride remover at a temperature that is above the dew point of the compressed effluent, yet below polymerization reaction temperatures of the compressed effluent, wherein the temperature at which the compressed effluent is introduced into the chloride remover is between 93° C. and 300° C.;

adsorbing trace chloride contaminants present in the compressed effluent in the chloride remover with an adsorbent to provide a treated effluent; and cooling the treated effluent to produce a cooled treated effluent.

10. The process of claim 9, wherein the adsorbent comprises an activated alumina, a promoted alumina product, metal oxides, molecular sieves, or combinations thereof.

11. The process of claim 9, wherein adsorbing the trace chloride contaminants takes place at a pressure between about 345 kPa to 2750 kPa.

12. The process of claim 9, wherein adsorbing the trace chloride contaminants comprises physical adsorption, chemisorption, or a combination thereof.

13. The process of claim 9, further comprising:
introducing the cooled treated effluent to a drier;
wherein cooling the treated effluent takes place downstream of the chloride remover and upstream of the drier.

14. The process of claim 13, further comprising:
separating an olefin product, an unconverted paraffin, and a recycle hydrogen stream from an output stream of the drier;
recovering the olefin product; and
recycling the recycle hydrogen stream and the unconverted paraffin to the dehydrogenation reaction zone.

* * * * *